United States Patent [19]
Levesque

[11] Patent Number: 5,366,451
[45] Date of Patent: Nov. 22, 1994

[54] DISPOSABLE ABSORBENT PRODUCT

[75] Inventor: Yvon Levesque, Montreal, Canada

[73] Assignee: Johnson & Johnson Inc., Montreal, Canada

[21] Appl. No.: 739,936

[22] Filed: Aug. 2, 1991

[51] Int. Cl.$^5$ .............................................. A61F 13/15
[52] U.S. Cl. .................... 604/378; 604/379; 604/383
[58] Field of Search ........................ 604/378–383, 604/358, 385.1, 368

[56] References Cited

U.S. PATENT DOCUMENTS 4,988,344  1/1991  Reising et al. ...................... 604/368

FOREIGN PATENT DOCUMENTS 163680    9/1988  European Pat. Off. ........ A61F 5/44
316771A2  5/1989  European Pat. Off. ..... A61F 13/18
WO90/14814 12/1990 WIPO ..................... A61F 13/18

Primary Examiner—Randall L. Green
Assistant Examiner—Rob Clarke

[57] ABSTRACT

A composite absorbent structure capable of extremely short fluid penetration time, well-suited for use as an absorbent core in disposable absorbent products such as adult disposable briefs, diapers, incontinence pads, sanitary napkins, wound dressings and bandages. The composite absorbent structure comprises a highly absorbent fluid transfer sheet having a low fluid retentiveness, and a laminated, wicking reservoir with a high fluid retentiveness in intimate fluid communication with the fluid transfer sheet to draw fluid therefrom under the effect of capillary action. The laminated reservoir includes superposed layers, the layer closest to the fluid transfer sheet being provided with a fluid distribution well. A highly porous and hydrophilic spacer element is inserted between the reservoir layers establishing a high void volume area which forms an extension of the fluid absorptive well between the reservoir layers. The invention also comprehends a method for providing a rapid fluid absorption in a disposable absorbent product.

49 Claims, 4 Drawing Sheets

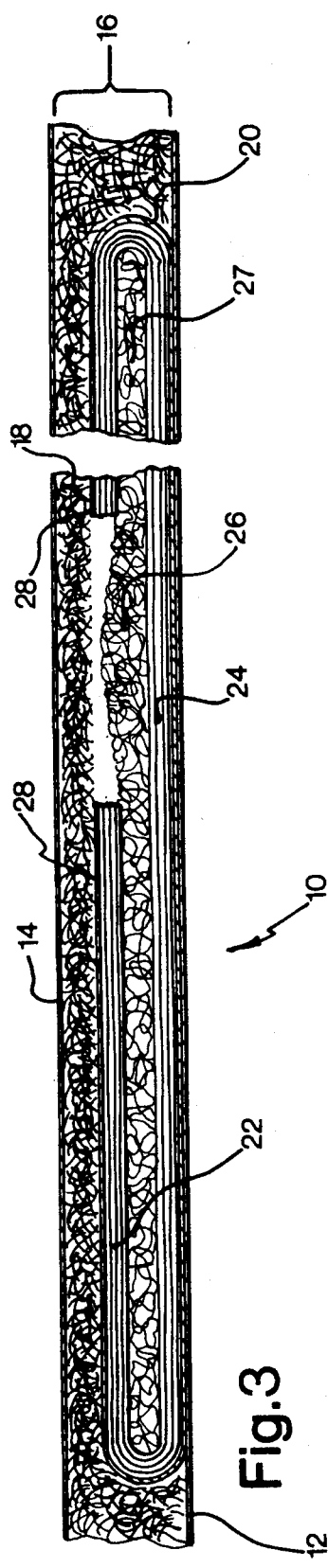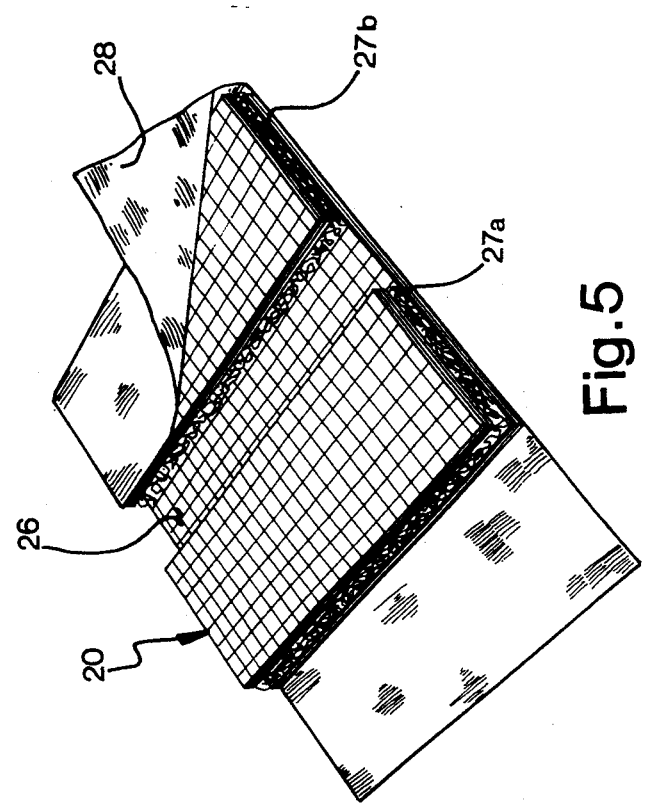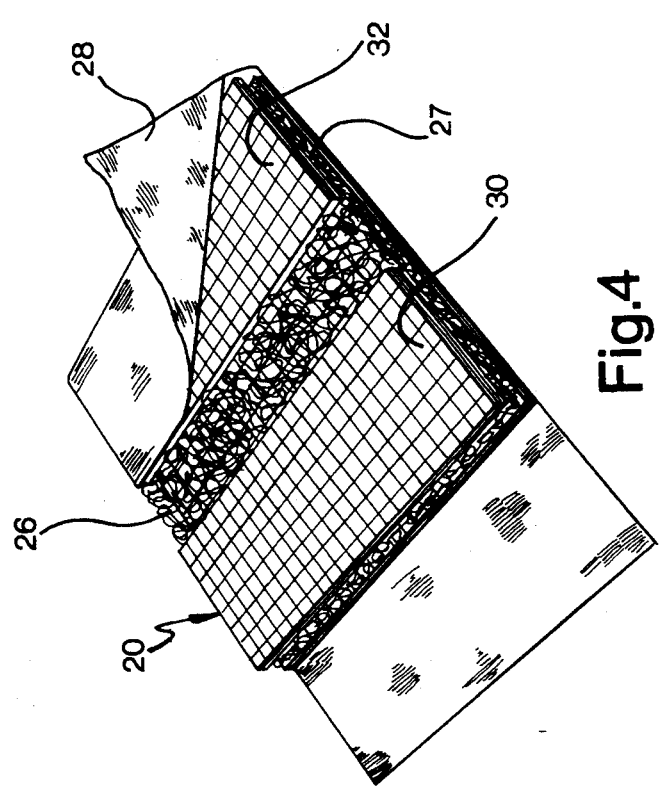

DISPOSABLE ABSORBENT PRODUCT

FIELD OF THE INVENTION

The invention relates to the general field of disposable fluid absorbent products, more particularly, to a composite absorbent structure having the ability to rapidly take-up fluid. The invention also relates to a method for providing rapid fluid absorption in a composite absorbent structure which combines a fluid transfer sheet and a laminated reservoir.

BACKGROUND OF THE INVENTION

Absorbent structures used in diapers, incontinence products and the like, must have the ability to rapidly take-up and retain body fluids which are released in an appreciable quantity over a relatively short period of time. To achieve this objective, the absorbent structure should be able to rapidly capture the onrush of fluid to prevent the fluid to leak past the edges of the absorbent structure, disperse by wicking action the captured fluid mass within the entire available absorbent volume, and lock the absorbed fluid therein to prevent leak-through and wet-back failures.

An absorbent structure which has been found particularly successful in this regard is a combination of a highly permeable fluid transfer sheet, such as pulp, exhibiting an extremely short fluid penetration time, and a highly absorbent and wicking laminated reservoir, made from peat moss material for example, in intimate fluid communicative relationship with the fluid transfer sheet, whose purpose is to permanently retain the absorbed fluid. This composite absorbent structure combines the desirable advantages of fairly rapid fluid penetration, high absorption and excellent wicking power contributing to reduce failures.

To further enhance the fluid absorption characteristics of the composite absorbent structure, it has been suggested to provide the laminated reservoir with a fluid distribution well in the inner reservoir layer. (For the purpose of this specification, the terms "inner layer" and "outer layer" will be used to designate the various layers of the laminated reservoir by their positions with respect to the fluid transfer sheet. "Inner" denotes a position closer to the fluid transfer sheet, while "outer" refers to a position farther from the fluid transfer sheet). The purpose of the well is twofold. Firstly, it exposes the outer layer to the fluid transfer sheet, through an opening in the inner layer, thereby increasing the surface area of the laminated reservoir capable to take-up fluid. Secondly, the well has the ability to distribute a coherent mass of fluid released from the fluid transfer sheet, along the laminated reservoir from the point of impact to prevent local saturation and overflow leakage.

Although composite absorbent structures of the type described above perform relatively well, it is desirable to further improve their fluid absorption characteristics.

OBJECTS AND STATEMENT OF THE INVENTION

An object of the invention is to provide a composite absorbent structure which combines a fluid transfer sheet and a laminated reservoir, having good fluid absorption and an advantageously short fluid penetration time.

Another object of the invention is a method to provide a good fluid absorption and an advantageously short fluid penetration time in a composite absorbent structure which combines a fluid transfer sheet and a laminated reservoir.

A further object of the invention is to provide a disposable absorbent product with a composite absorbent structure combining a fluid transfer sheet and a laminated reservoir, having good fluid absorption and an advantageously short fluid penetration time.

The present inventor has made the unexpected discovery that when providing a highly porous and hydrophilic element between the inner and the outer layers of the laminated reservoir, a considerable improvement in the fluid absorption characteristics is obtained, by virtue of a reduction in the fluid penetration time of the laminated reservoir. The highly porous and hydrophilic element is virtually transparent to fluid in a state of motion, while forming a physical spacer between the absorptive layers of the laminated reservoir allowing fluid discharged in the fluid distribution well to flow and spread deeply between the absorptive layers. The resultant increase in the effective absorbent surface of the laminated reservoir contributes to reduce the fluid take-up time.

In contrast, a conventional composite absorbent structure without such a porous and hydrophilic element between the absorbent layers of the laminated reservoir suffers from a slower fluid penetration time because the absorbent layers are in intimate contact with each other and fluid cannot directly penetrate therein.

The absorbent structure according to the invention is well suited for use in disposable absorbent products such as adult disposable briefs, diapers, incontinence pads, sanitary napkins, wound dressings, bandages and the like.

In view of the foregoing, the invention as embodied and described herein provides a composite absorbent structure, comprising,
- a highly absorbent fluid transfer sheet with a low fluid retentiveness;
- a laminated, wicking reservoir with a high fluid retentiveness in intimate fluid communication with the fluid transfer sheet to draw fluid therefrom by capillary action (for the purpose of this specification, "capillary action" is defined as the ability of fluid to move toward or within a given material as a result of capillary attraction) the laminated reservoir including superposed inner and outer layers, the inner layer being located between the outer layer and the fluid transfer sheet and including a recessed area constituting a fluid distribution well, a highly porous and hydrophilic spacer element between the layers establishing a high void volume zone forming an extension of the fluid distribution well between the layers.

In a preferred embodiment, the recessed area is an opening extending through the inner layer of the laminated reservoir.

As embodied and broadly described herein, the invention also comprises a method for providing a relatively short penetration time in a composite absorbent structure of the type comprising,
- a highly absorbent fluid transfer sheet with a low fluid retentiveness;
- a wicking, laminated reservoir with a high fluid retentiveness in intimate fluid communication with the fluid transfer sheet to draw fluid therefrom by capillary action, the laminated reservoir including superposed inner and outer layers, the inner layer being located between the outer layer and the fluid transfer sheet and including a recessed area preferably an opening in the inner layer, constituting a fluid distribution well, the method comprising the step of providing between the inner and outer layers a highly porous and hydrophilic spacer element establishing a high void volume area therebetween forming an extension of the fluid distribution well between the layers.

In a preferred embodiment, the highly porous and hydrophilic spacer element has a density in the range of about 0.005 to 0.08 grams per cubic centimeter (g/cc), more preferably in the range of about 0.01 to 0.04 g/cc, and most preferably in the range of about 0.01 to 0.02 g/cc. The dry thickness of the highly porous and hydrophilic spacer element is preferably in the range of about 0.01 to 0.5 inches measured at 2.8 grams per centimeter squared (g/cm$^2$) pressure, more preferably in the range of about 0.03 to 0.3 inches measured at 2.8 g/cm$^2$ pressure, and most preferably in the range of about 0.05 to 0.25 inches measured at 2.8 g/cm$^2$ pressure.

In a preferred embodiment, the laminated reservoir is a unitary sheet of absorbent material folded in a C-configuration forming the superposed inner and outer layers, the fluid distribution well in the inner layer being defined between the spaced apart folded edges of the absorbent material. In a variant, the layers of the laminated reservoir are physically separate, the inner layer being formed by two strips overlaying the outer layer, and being in a spaced apart relationship to define therebetween the fluid distribution well.

In a preferred embodiment, the highly porous and hydrophilic spacer element is a unitary sheet-like structure inserted between the inner and outer layers, the fluid distribution well on the inner layer exposing the central portion of the spacer element. In a variant, the spacer element is formed by a pair of strips in a spaced apart relationship extending on either side of the fluid distribution well.

In a most preferred embodiment, the fluid transfer sheet and the highly porous and hydrophilic spacer element are made of pulp fluff material, and the laminated reservoir is made of peat moss composite material. In a variant, the hydrophilic spacer element is made from a web of randomized polyester and bi-component fibers treated with a wetting agent, an open pore foam of cellulose material, high bulk fiberfill type thermally bonded material, cross-linked cellulosic pulp and mixtures of heat stabilized synthetic pulp.

As embodied and broadly described herein, the invention also relates to a disposable absorbent product comprising the composite absorbent structure according to the invention mounted in an envelope constituted by a fluid permeable cover layer extending over the fluid transfer sheet and a fluid impermeable backing layer under the laminated reservoir to arrest any fluid which may leak from the laminated reservoir.

BRIEF DESCRIPTION OF THE DRAWINGS

FIG. 3 is an enlarged vertical cross-sectional view of the adult disposable brief shown in FIG. 1;

FIG. 4 is a perspective view of the laminated reservoir of the composite absorbent structure according to a first variant;

FIG. 5 is a perspective view of the laminated reservoir of the composite absorbent structure according to a second variant.

DESCRIPTION OF PREFERRED EMBODIMENTS

Reference will now be made in detail to preferred embodiments of the invention, specific examples of which are illustrated in the following examples sections.

To achieve the object of improving the fluid penetration time of a composite fluid absorbent structure which combines a fluid transfer sheet and a laminated reservoir with a fluid distribution well in the inner layer of the laminated reservoir, the present inventor has made the unexpected discovery that a highly porous and hydrophilic sheet incorporated between the inner and outer layers of the laminated reservoir enhances the ability of the laminated reservoir to rapidly absorb fluid by forming an extension of the fluid distribution well between the layers of the laminated reservoir. In use, a coherent mass of fluid which is being discharged from the fluid transfer sheet toward the laminated reservoir will flow in the fluid distribution well and immediately will penetrate between the layers of the laminated reservoir. The fluid penetration time of the laminated reservoir is considerably reduced by virtue of the larger surface area of the laminated reservoir now available to absorb fluid.

Figure 1:
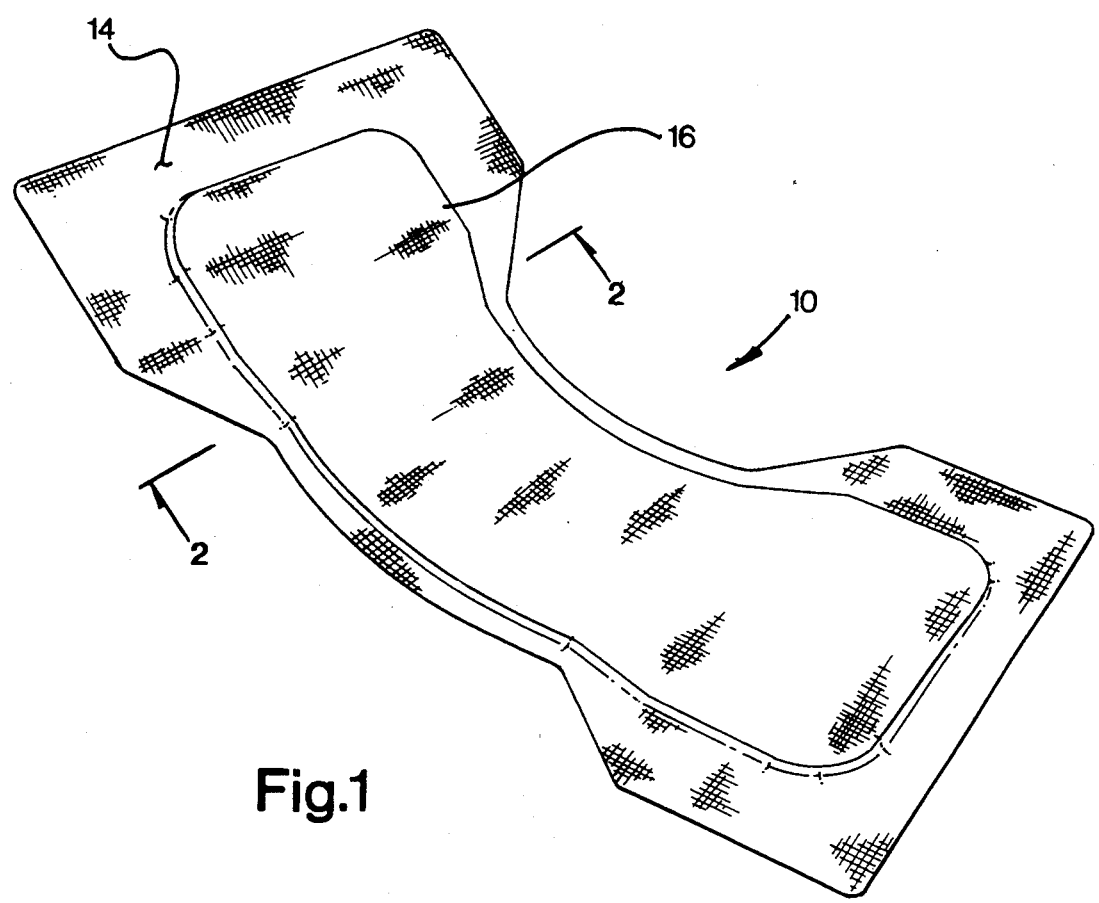
FIG. 1 is a perspective view of an adult disposable brief with a composite absorbent structure according to the present invention.
Figure 2:
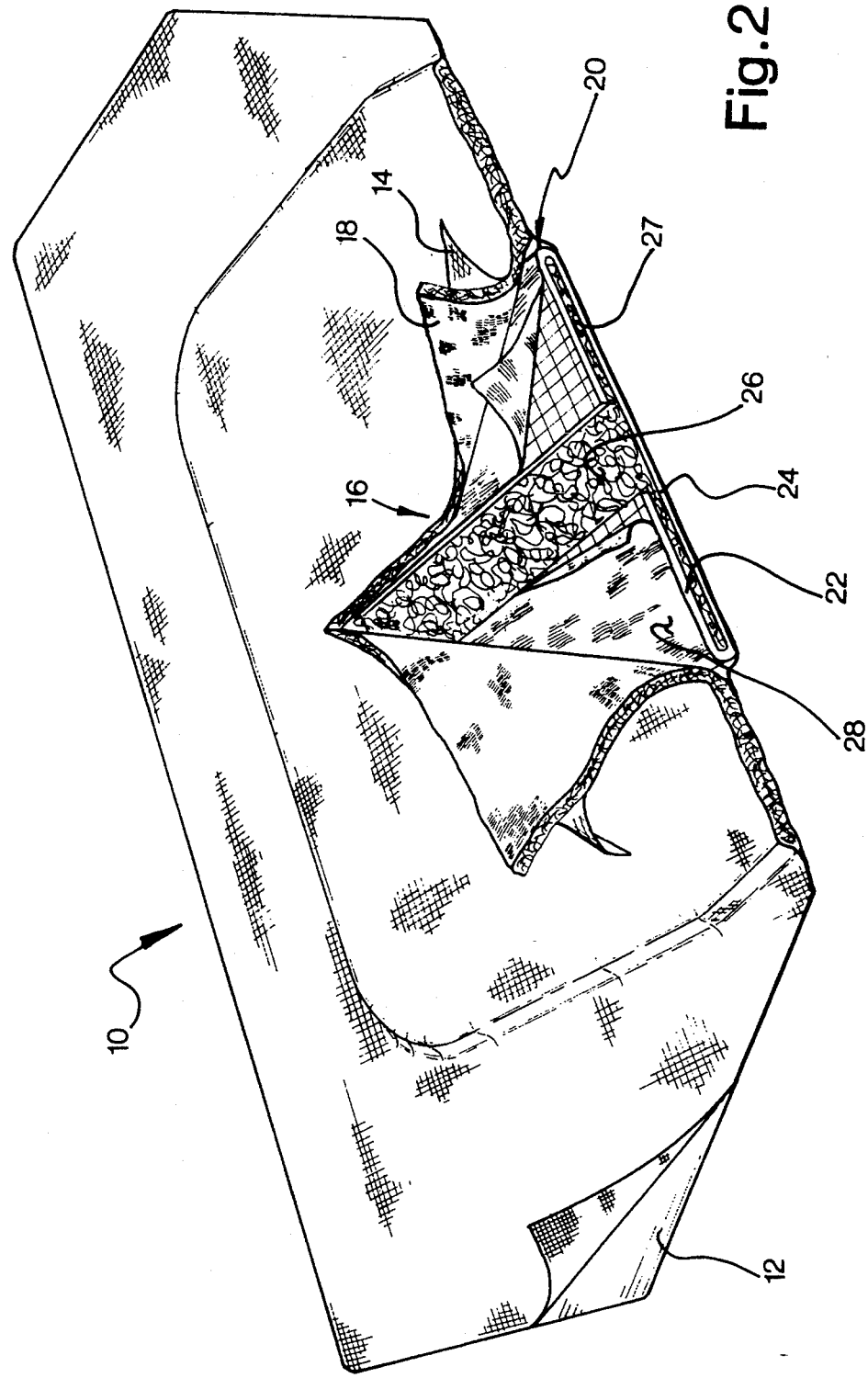
FIG. 2 is a sectional view in perspective taken along lines 2—2 of FIG. 1.

FIGS. 1, 2 and 3 illustrate an adult disposable brief incorporating a composite absorbent structure according to the invention. The adult disposable brief designated comprehensively by the reference numeral 10 comprises an impermeable backing layer 12, a highly permeable cover layer 14 and an improved composite absorbent structure 16 held captive between layers 12 and 14. The composite absorbent structure 16 comprises a highly absorbent fluid transfer sheet 18 co-extensive with layers 12 and 14 except at their marginal portions. Under the fluid transfer sheet 18 is inserted a laminated reservoir 20 in the form of a unitary sheet of absorbent material folded in a C-shaped configuration, displaying inner and outer superposed layers 22 and 24 respectively. The inner layer 22 is formed by the folded lateral edges of the unitary absorbent sheet which are in a spaced apart relationship defining therebetween a fluid distribution well 26 extending along the entire length of the laminated reservoir 20.

Between the layers 22 and 24 is inserted a relatively thin sheet 27 of a highly porous and hydrophilic material forming a spacer, separating layers 22 and 24 from one another and defining therebetween a high void volume zone which has the effect of extending the well 26 deeply within the laminated reservoir 20, between layers 22 and 24.

The laminated reservoir 20 is covered with a thin and highly fluid permeable wadding 28 for the purpose of enhancing the structural integrity and stability of the laminated reservoir 20 without interfering with the fluid absorption process. The wadding 28 prevents the absorbent material of the laminated reservoir 20 from disintegrating or locally rupturing under the effect of mechanical stress applied during the automated assembly of the adult disposable brief or when the adult disposable brief is in use, in the wet or in the dry state. In a most preferred embodiment, the wadding 28 is a non-woven fabric.

In a first variant, shown in FIG. 4, the inner layer of the laminated reservoir 20 is physically separated from the outer layer and it is formed by a pair of strips 30,32 in a spaced apart relationship to define therebetween the fluid distribution well 26. In this embodiment, the wadding 28 forms an internal structural envelope retaining together all the components of the laminated reservoir 20.

In a second variant, shown in FIG. 5, the highly porous and hydrophilic sheet 27 is formed by two separate strips 27a and 27b extending on either side of the fluid distribution well 26.

The fluid absorption process of the composite absorbent structure according to the invention will now be described. Fluid which is being discharged on the absorbent surface of the adult disposable brief 10, will freely flow through the fluid permeable cover layer 14 and will penetrate the fluid transfer sheet 18. The fluid penetration rate in the fluid transfer sheet 18 is high due to its highly porous structure, thus reducing the possibility of fluid leaking past the edges of the adult disposable brief by failure of the fluid transfer sheet 18 to rapidly capture the fluid discharge. For applications where the rate of fluid release is sudden and high, the ability of the composite absorbent structure to capture fluid on contact is particularly important, reducing considerably the likelihood of failure. Urinary incontinence is an example where the onrush of body fluid can be contained only by an absorbent structure which exhibits an ultra short fluid penetration time. A highly porous fibrous network has been found particularly advantageous in this respect because discharged fluid can easily and rapidly be absorbed due to the large interfiber distances of the fibrous network.

Although the fluid transfer sheet 18 is capable of rapid fluid absorption, it lacks the ability to retain the absorbed fluid within the network of distant fibers. When the fluid transfer sheet is below the saturation level, fluid migrates from the fluid transfer sheet toward the laminated reservoir by capillary action as a result of the substantial difference in wicking power therebetween. Such fluid migration is slow and well controlled, occurring at the rate of fluid acceptance of the laminated reservoir 20.

When an onrush of fluid occurs on the fluid transfer sheet 18, the controlled migration process is disturbed because the fluid mass released on the composite absorbent structure strikes through the fluid transfer sheet 18 and accumulates as a coherent body on the laminated reservoir 20. The fluid distribution well 26 acts as a temporary fluid containment system to prevent overflow leakage while dispersing the fluid along the laminated reservoir, spreading the fluid over a larger absorbent surface to accelerate the fluid penetration process in the laminated reservoir.

The highly porous and hydrophilic spacer sheet 27 greatly enhances the ability of the fluid distribution well 26 to contain and disperse fluid by increasing the capacity of the well and augmenting the absorbing surface through which the process of fluid take-up in the laminated reservoir is carried out. In contrast to prior art composite absorbent structures where the fluid distribution well is small, the present invention provides a considerably larger well extending deeply between the inner and the outer layers to make a more efficient use of the available fluid absorbing surface, thus reducing the fluid penetration time in the laminated reservoir.

EXAMPLES

The invention will now be illustrated by examples. The examples are not intended to be limiting of the scope of the present invention but, read in conjunction with the detailed and general description above, provide a further understanding of the present invention. The description of the various test procedures to which the composite absorbent structures of the following examples have been subjected are described in the section entitled "Test Procedures" following Table I.

EXAMPLE 1

Prior art composite absorbent structure with a laminated reservoir without a fluid distribution well in the inner layer and without a spacer sheet between the layers.

| COVER LAYER: | Non-woven fabric with Enka fibers (fibers commercialized by BASF Company) |
| --- | --- |
| Basis weight (g/m$^2$): | 25 |
| Density (g/cc): | 0.02 |
| Total weight (g): | 1.2 |
| Dimensions (in.) | 5 × 15 |

| FLUID TRANSFER SHEET: | Two plies wood pulp fluff |
| --- | --- |
| Basis weight (g/m$^2$): | 130 (per ply) |
| Density (g/cc): | 0.05 |
| Total weight (g): | 12.5 g |
| Dimensions (in.): | 5 × 15 |

| LAMINATED RESERVOIR: | Two superposed layers of peat moss composite material |
| --- | --- |
| Basis weight per ply (g/m$^2$): | 425 |
| Density (g/cc): | 0.2 |
| Total weight (g): | 41.5 |
| Dimensions (in.): | 5 × 15 |

BACKING LAYER: Polyethylene sheet

EXAMPLE 2

Prior art composite absorbent structure with C-folded laminated reservoir without spacer sheet.

| COVER LAYER: | Non-woven fabric with Enka fibers (fibers commercialized by BASF Company) |
| --- | --- |
| Basis weight (g/m$^2$): | 25 |
| Density (g/cc): | 0.02 |
| Total weight (g): | 1.2 |
| Dimensions (in.) | 5 × 15 |

| FLUID TRANSFER SHEET: | Two plies wood pulp fluff |
| --- | --- |
| Basis weight (g/m$^2$): | 130 (per ply) |
| Density (g/cc): | 0.05 |
| Total weight (g): | 12.5 g |
| Dimensions (in.): | 5 × 15 |

| LAMINATED RESERVOIR: | Peat moss composite sheet folded in a C-shaped configuration with a one inch wide fluid distribution well in the inner layer |
|---|---|
| basis weight per ply (g/m$^2$): | 425 |
| Density (g/cc): | 0.2 |
| Total weight (g): | 37.0 |
| Dimensions (in.): | 9 × 15 |

BACKING LAYER, Polyethylene sheet.

EXAMPLE 3

Composite absorbent structure according to the invention, constructed as shown in FIGS. 1, 2 and 3.

| COVER LAYER: | Non-woven fabric with Enka fibers (fibers commercialized by BASF Company) |
|---|---|
| Basis weight (g/m$^2$): | 25 |
| Density (g/cc): | 0.02 |
| Total weight: | 1.2 |
| Dimensions | 5 × 15 |

| FLUID TRANSFER SHEET: | Single ply wood pulp fluff |
|---|---|
| Basis weight (g/m$^2$): | 130 |
| Density (g/cc): | 0.05 |
| Total weight (g): | 6.2 |
| Dimensions (in.) | 5 × 15 |

| LAMINATED RESERVOIR: | Peat moss composite sheet folded in a C-shaped configuration with a one inch wide fluid distribution well in the inner layer |
|---|---|
| Basis weight per ply (g/m$^2$): | 425 |
| Density (g/cc): | 0.2 |
| Total weight (g): | 37.0 |
| Dimensions (in.): | 9 × 15 |

| SPACER SHEET: | Single ply wood pulp fluff |
|---|---|
| Basis weight (g/m$^2$): | 130 |
| Density (g/cc): | 0.05 |
| Total weight (g): | 6.2 |
| Dimensions (in.) | 5 × 15 |

BACKING LAYER: Polyethylene Sheet

EXAMPLE 4

Composite absorbent structure according to the invention.

| COVER LAYER: | Non-woven fabric with Enka fibers (fibers commercialized by BASF Company) |
|---|---|
| Basis weight (g/m$^2$): | 25 |
| Density (g/cc): | 0.02 |
| Total weight (g): | 1.2 |
| Dimensions (in.): | 5 × 15 |

| FLUID TRANSFER SHEET: | Single ply wood pulp fluff |
|---|---|
| Basis weight (g/m$^2$): | 130 |
| Density (g/cc): | 0.05 |
| Total weight (g): | 6.2 |
| Dimensions (in.): | 5 × 15 |

| LAMINATED RESERVOIR: | Peat-moss composite sheet folded in a C-shaped configuration with one inch wide fluid distribution well in the inner layer |
|---|---|
| Basis weight per ply (g/m$^2$): | 425 |
| Density (g/cc): | 0.2 |
| Total weight (g): | 37.0 |
| Dimensions (in.): | 9 × 15 |

| SPACER SHEET: | Two spaced apart strips of one ply wood pulp fluff on either side of the fluid distribution well |
|---|---|
| Basis weight (g/m$^2$): | 130 |
| Density (g/cc): | 0.05 |
| Weight of each strip (g): | 5.5 |
| Dimensions of each strip (in.): | 2 × 15 |

BACKING LAYER: Polyethylene sheet

EXAMPLE 5

Composite absorbent structure according to the invention, as shown in FIGS. 1, 2 and 3.

| COVER LAYER: | Non-woven fabric with Enka fibers (fibers commercialized by BASF Company) |
|---|---|
| Basis weight (g/m$^2$): | 25 |
| Density (g/cc): | 0.02 |
| Total weight (g): | 1.2 |
| Dimensions (in.): | 5 × 15 |

| FLUID TRANSFER SHEET: | Single ply wood pulp fluff |
|---|---|
| Basis weight (g/m$^2$): | 130 |
| Density (g/cc): | 0.05 |
| Total weight (g): | 6.2 |
| Dimensions (in.): | 5 × 15 |

| LAMINATED RESERVOIR: | Peat moss composite sheet in a C-folded configuration with a one inch wide fluid distribution well in the inner layer |
|---|---|
| Basis weight per ply (g/m$^2$): | 425 |
| Density (g/cc): | 0.2 |
| Total weight (g): | 37.0 |
| Dimensions (in.): | 9 × 15 |

| SPACER SHEET: | Composite web of randomized polyester (6 dpf (denier per fiber) and bi-component fibers (3.8 dpf) in 75:25 ratio, sprayed with 0.10% solution of GR-5 (trademark) wetting agent manufactured by the Rohm and Haas Company, U.S.A. |
|---|---|
| Basis weight (g/m$^2$): | 30 |

-continued

| SPACER SHEET: | Composite web of randomized polyester (6 dpf (denier per fiber) and bi-component fibers (3.8 dpf) in 75:25 ratio, sprayed with 0.10% solution of GR-5 (trademark) wetting agent manufactured by the Rohm and Haas Company, U.S.A. | |
|---|---|---|
| Density (g/cc): | | 0.015 |
| total weight (g): | | 1.5 |
| Dimensions (in.): | | 5 × 15 |

BACKING LAYER: Polyethylene sheet

EXAMPLE 6

Composite absorbent structure according to the invention, constructed as shown in FIGS. 1, 2 and 3.

| COVER LAYER: | Non-woven fabric with Enka fibers (fibers commercialized by BASF Company) | |
|---|---|---|
| Basis weight (g/m$^2$): | | 25 |
| Density (g/cc): | | 0.02 |
| Total weight (g): | | 1.2 |
| Dimensions (in.): | | 5 × 15 |

| FLUID TRANSFER SHEET: | Single ply wood pulp fluff | |
|---|---|---|
| Basis weight (g/m$^2$): | | 130 |
| Density (g/cc): | | 0.05 |
| Total weight (g): | | 6.2 |
| Dimensions (in.): | | 5 × 15 |

| LAMINATED RESERVOIR: | Peat moss composite sheet in a C-folded configuration with a one inch wide fluid distribution well in the inner layer | |
|---|---|---|
| Basis weight per ply (g/m$^2$): | | 425 |
| Density (g/cc): | | 0.2 |
| Total weight (g): | | 37.0 |
| Dimensions (in.): | | 9 × 15 |

| SPACER SHEET: | Carded viscose rayon web (1.5 dpf) | |
|---|---|---|
| Basis weight (g/m$^2$): | | 70 |
| Density (g/cc): | | 0.088 |
| Total weight (g): | | 3.25 |
| Dimensions (in.): | | 5 × 15 |

BACKING LAYER, Polyethylene sheet

The composite absorbent structures according to examples 1–6 were tested for:
a) fluid penetration time
b) fluid advance within the laminated reservoir; and
c) free surface wetness.

The results are summarized in Table I

TABLE 1

| | Example 1 | Example 2 | Example 3 | Example 4 | Example 5 | Example 6 |
|---|---|---|---|---|---|---|
| Fluid penetration time (seconds) | 26 | 25 | 22.5 | 17 | 11 | 32 |
| Fluid advance within laminated reservoir (inches) | 13 | 13 | 13.6 | 14 | 14.3 | 14 |
| Free surface wetness (percentage %) | 165 | 170 | 135 | 130 | 130 | 130 |

DESCRIPTION OF TEST PROCEDURES a) BASIS WEIGHT

Purpose: To determine the basis weight of the absorbent material.

Test procedure: One square foot sample is weighted and the basis weight is calculated in grams per meter squared (g/m$^2$).

b.) DENSITY

Purpose: To determine the density of an absorbent material.

Test procedure: The density of the processed material is obtained by taking the weight of a 2 inch × 3 inch sample and dividing it by its volume (thickness × area of sample). For pulp fluff material, the thickness of the sample is measured at 2.8 g/cm$^2$ pressure.

c) FLUID PENETRATION TIME

Purpose: To determine the penetration time of an absorbent material by measuring the time required to completely absorb a finite amount of fluid.

Figure 6:
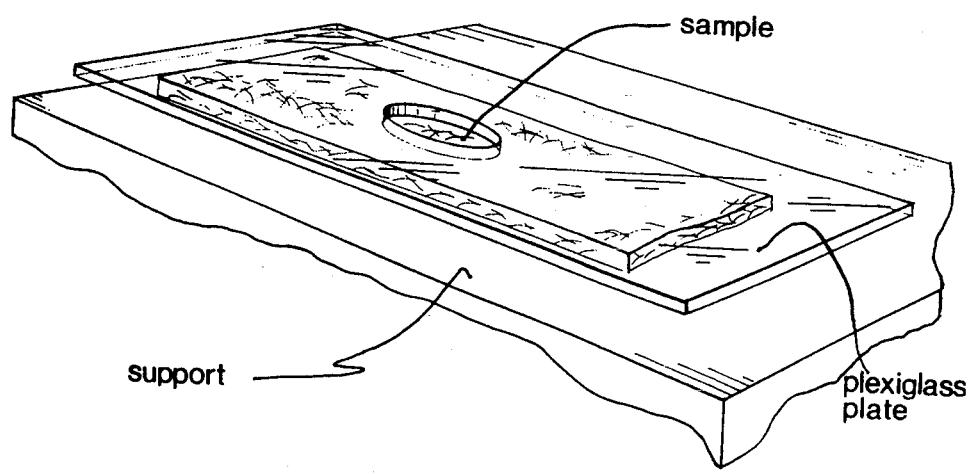
FIG. 6 is a perspective view of a set-up for conducting a fluid penetration time test procedure.

Test procedure: The time required for a sample under 2.8 g/cm$^2$ pressure covered by a plexiglass plate, as shown in FIG. 6, to absorb 5.45 cc/g of test fluid fed to the sample through an oval orifice on the plate measuring 9 × 3 centimeters. The penetration time is recorded when all free liquid has disappeared from the surface of the sample exposed by the oval orifice.

Test Fluid: 1% NaCl solution.

d) FLUID ADVANCE WITHIN THE LAMINATED RESERVOIR

Purpose: To determine the ability of an absorbent material to disperse fluid within its structure by measuring the distance travelled by a finite amount of fluid deposited on the absorbent material.

Test Procedure: 5.45 cc/g of test fluid based on the weight of the sample of absorbent material is delivered on the sample. The distance travelled by the fluid form the point of impact is recorded after 15 minutes.

Test Fluid: 1% NaCl solution.

e) FREE SURFACE WETNESS AT POINT OF FLUID IMPACT

Purpose: To determine the ability of an absorbent material to pull fluid within its structure.

Test procedure, A NuGauze (trademark of Johnson & Johnson Inc.) sponge is placed under the cover layer of the composite absorbent structure and under a load of 50 g, 15 minutes after a discharge of 5.45 cc/g of test fluid based on the weight of absorbent material has been delivered on the absorbent structure. The liquid pick-up in the sponge is measured in percentage based on its dry weight. The liquid pickup measurement is an indication of the amount of fluid remaining at the fluid impact point on the absorbent structure.

Test Fluid: 1% NaCl solution

DISCUSSION

For a better understanding of the invention, the test results in Table I will be discussed. By comparing the fluid penetration times of prior art absorbent structures according to Examples 1 and 2, it can be observed that the configuration of the laminated reservoir greatly influences its absorption characteristics. The provision of a fluid distribution well in the inner layer results in a considerable reduction of the fluid penetration time.

A significant improvement in the fluid penetration time over these prior art absorbent structures is obtained by the use of a low density, highly porous and hydrophilic spacer sheet between the layers of the laminated reservoir. The density of the spacer sheet is particularly important and greatly influences the fluid penetration time. The best results are obtained by the absorbent structure of Example 5, which has the lowest spacer sheet density. In Example 6, the increase in density of the spacer sheet adversely affects the fluid penetration time. An absorbent structure constructed in accordance with Example 6 may not necessarily have practical applications due to its poorer performance; it serves only the purpose of illustrating the relationship between the density of the spacer sheet and fluid penetration time.

In addition to improving the fluid penetration time, the use of a spacer sheet also helps in drying out the impact point more quickly as indicated by the results of the free surface wetness of the point of impact and by the results of fluid advance within the laminated reservoir layer.

Please provide a short discussion of the results of fluid advance within the laminated reservoir.

The scope of the present invention is not limited by the description, examples and suggestive uses herein and modifications can be made without departing from the spirit of the invention.

The composite absorbent structure of the present invention may also be utilized in diverse products including incontinence pads, adult disposable briefs, diapers, sanitary napkins or tampons, or as desiccants for use in packaging materials to keep goods dry during shipping or storage. Applications of the product and methods of the present invention for sanitary and other health care uses can be accomplished by any sanitary protection, incontinence, medical, and absorbent methods and techniques as are presently or prospectively known to those skilled in the art. Thus it is intended that the present invention cover the modifications and variations of this invention provided that they come within the scope of the appended claims and their equivalents.

I claim:

1. A composite absorbent structure, comprising:
   a cover sheet;
   a highly absorbent fluid transfer sheet with a low fluid retentiveness; and
   a wicking, laminated reservoir wherein said fluid transfer sheet is located between said reservoir and said cover sheet said reservoir, having a high fluid retentiveness in fluid communication with said fluid transfer sheet to draw fluid therefrom by capillary action, said laminated reservoir including superposed inner and outer layers, said inner layer being located between said outer layer and said fluid transfer sheet and including a recessed area defining a fluid distribution well, a highly porous and hydrophilic spacer element between said layers establishing a high void volume area which forms an extension of said fluid distribution well between said layers.

2. A composite absorbent structure as defined in claim 1, wherein said highly porous and hydrophilic spacer element has a density in the range of about 0.005 to 0.08 g/cc.

3. A composite absorbent structure as defined in claim 1, wherein said highly porous and hydrophilic spacer element has a density in the range of about 0.01 to 0.04 g/cc.

4. A composite absorbent structure as defined in claim 1, wherein said highly porous and hydrophilic spacer element has a density in the range of about 0.01 to 0.02 g/cc.

5. A composite absorbent structure as defined in claim 1, wherein said highly porous and hydrophilic spacer element has a dry thickness in the range of about 0.01 to 0.5 inches measured at 2.8 g/cm$^2$ pressure.

6. A composite absorbent structure as defined in claim 1, wherein said highly porous and hydrophilic spacer element has a dry thickness in the range of about 0.030 to 0.3 inches measured at 2.8 g/cm$^2$ pressure.

7. A composite absorbent structure as defined in claim 1, wherein said highly porous and hydrophilic spacer element has a dry thickness in the range of about 0.05 to 0.25 inches measured at 2.8 g/cm$^2$ pressure.

8. A composite absorbent structure as defined in claim 1, wherein said laminated reservoir has a C-folded configuration.

9. A composite absorbent structure as defined in claim 1, wherein said layers are separate from one another.

10. A composite absorbent structure as defined in claim 1, wherein said inner layer comprises two strips in a spaced apart configuration defining therebetween said recessed area.

11. A composite absorbent structure as defined in claim 1, wherein said highly porous and hydrophilic spacer element is a unitary sheet-like structure.

12. A composite absorbent component as defined in claim 1, wherein said highly porous and hydrophilic spacer element comprises a pair of strips in a spaced apart relationship extending on either side of said fluid distribution well.

13. A composite absorbent structure as defined in claim 1, wherein said fluid transfer sheet comprises wood pulp fluff material.

14. A composite absorbent structure as defined in claim 1, wherein said laminated reservoir comprises composite peat moss material.

15. A composite absorbent structure as defined in claim 1, wherein said highly porous hydrophilic spacer element contains a material selected from the group consisting of wood pulp fluff, a composite web of randomized polyester and bi-component fibers treated with a wetting agent, open pore cellulose foam, high bulk material selected from the class comprising fiberfill, cross-linked cellulosic pulp, a blend of heat stabilized synthetic pulp and mixtures thereof.

16. A composite absorbent structure as defined in claim 1, wherein said recessed area is an opening through said inner layer.

17. A disposable absorbent product comprising:
a fluid permeable cover;
an impervious backsheet; and
a composite absorbent structure between said fluid permeable cover and said impervious backsheet, said composite absorbent structure including:
a highly absorbent fluid transfer sheet with a low fluid retentiveness;
a wicking, laminated reservoir having a high fluid retentiveness in fluid communication with said fluid transfer sheet to draw fluid therefrom by capillary action, said laminated reservoir including superposed inner an outer layers, said inner layer being located between said outer layer and said fluid transfer sheet and including a recessed area defining a fluid distribution well, a highly porous and hydrophilic spacer element between said layers establishing a high void volume area forming an extension of said well between said layers.

18. A disposable absorbent product as defined in claim 17, wherein said highly porous and hydrophilic spacer element has a density in the range of about 0.005 to 0.08 g/cc.

19. A disposable absorbent product as defined in claim 17, wherein said highly porous and hydrophilic spacer element has a density in the range of about 0.01 to 0.04 g/cc.

20. A disposable absorbent product as defined in claim 17, wherein said highly porous and hydrophilic spacer element has a density in the range of about 0.01 to 0.02 g/cc.

21. A disposable absorbent product as defined in claim 17, wherein said highly porous and hydrophilic spacer element has a dry thickness in the range of about 0.01 to 0.5 inches measured at 2.8 g/cm$^2$ pressure.

22. A disposable absorbent product as defined in claim 17, wherein said highly porous and hydrophilic spacer element has a dry thickness in the range of about 0.03 to 0.3 inches measured at 2.8 g/cm$^2$ pressure.

23. A disposable absorbent product as defined in claim 17, wherein said highly porous and hydrophilic spacer element has a dry thickness in the range of about 0.05 to 0.25 inches measured at 2.8 g/cm$^2$ pressure.

24. A disposable absorbent product as defined in claim 17, wherein said laminated reservoir has a C-folded configuration.

25. A composite absorbent structure as defined in claim 17, wherein said layers are separate from one another.

26. A composite absorbent structure as defined in claim 17, wherein said inner layer comprises two strips in a spaced apart configuration defining therebetween said recessed area.

27. A disposable absorbent product as defined in claim 17, wherein said highly porous and hydrophilic spacer element comprises a pair of strips in a spaced apart relationship extending on either side of said fluid distribution well.

28. A disposable absorbent product as defined in claim 17, wherein said fluid transfer sheet comprises wood pulp fluff.

29. A disposable absorbent product as defined in claim 17, wherein said laminated reservoir comprises composite peat moss material.

30. A disposable absorbent product as defined in claim 17, wherein said highly porous hydrophilic spacer element contains a material selected from the group consisting of wood pulp fluff, a composite web of randomized polyester and bi-component fibers treated with a wetting agent, open pore cellulose foam, high bulk material selected from the class comprising fiberfill, cross-linked cellulosic pulp, a blend of heat stabilized synthetic pulp and mixtures thereof.

31. A disposable absorbent product as defined in claim 17, wherein said fluid permeable cover comprises a nonwoven fabric.

32. A disposable absorbent product as defined in claim 17, wherein said impervious backsheet comprises a polyethylene sheet.

33. A disposable absorbent product as defined in claim 17, wherein the disposable absorbent product is selected from the group consisting of diapers, adult briefs, incontinence products, sanitary napkins, wound dressings and bandages.

34. A composite absorbent structure as defined in claim 17, wherein said recessed area is an opening through said inner layer.

35. A method for reducing the fluid penetration time in a disposable absorbent product selected from the group consisting of incontinence products, diapers, adult briefs, sanitary napkins, wound dressings and bandages, comprising the step of incorporating in the disposable absorbent product a composite absorbent structure comprising:
a highly absorbent fluid transfer sheet with a low fluid retentiveness;
a wicking, laminated reservoir having a high fluid retentiveness in fluid communication with said fluid transfer sheet to draw fluid therefrom by capillary action, said laminated reservoir including superposed inner an outer layers, said inner layer being located between said outer layer and said fluid transfer sheet and including a recessed area defining a fluid distribution well, a highly porous and hydrophilic spacer element between said layers establishing a high void volume area forming an extension of said well between said layers.

36. The method of claim 35, wherein said highly porous and hydrophilic spacer element has a density in the range of about 0.005 to 0.08 g/cc.

37. The method of claim 35, wherein said highly porous and hydrophilic spacer element has a density in the range of about 0.01 to 0.04 g/cc.

38. The method of claim 35, wherein said highly porous and hydrophilic spacer element has a density in the range of about 0.01 to 0.02 g/cc.

39. The method of claim 35, wherein said highly porous and hydrophilic spacer element has a dry thickness in the range of about 0.01 to 0.5 inches measured at 2.8 g/cm$^2$ pressure.

40. The method of claim 35, wherein said highly porous and hydrophilic spacer element has a dry thickness in the range of about 0.03 to 0.3 inches measured at 2.8 g/cm$^2$ pressure.

41. The method of claim 35, wherein said highly porous and hydrophilic spacer element has a dry thickness in the range of about 0.05 to 0.25 inches measured at 2.8 g/cm$^2$ pressure.

42. The method of claim 35, wherein said highly porous and laminated reservoir has a C-folded configuration.

43. The method as defined in claim 35, wherein said layers of said composite absorbent structure are separate from one another.

44. The method as defined in claim 35, wherein said inner layer of said composite absorbent structure comprises two strips in a spaced apart configuration defining therebetween said recessed area.

45. The method of claim 35, wherein said highly porous and hydrophilic spacer element comprises a pair of strips in a spaced apart relationship extending on either side of said fluid distribution well.

46. The method of claim 35, wherein said fluid transfer sheet comprises wood pulp fluff material.

47. The method of claim 35, wherein said laminated reservoir comprises composite peat moss material.

48. The method of claim 35, wherein said highly porous hydrophilic spacer element contains a material selected from the group consisting of wood pulp fluff, a composite web of randomized polyester and bi-component fibers treated with a wetting agent, open pore cellulose foam, high bulk material selected from the class comprising fiberfill, cross-linked cellulosic pulp, a blend of heat stabilized synthetic pulp and mixtures thereof.

49. The method as defined in claim 35, wherein said recessed area of said composite absorbent structure is an opening through said inner layer.

* * * * *